(12) United States Patent
Knappe et al.

(10) Patent No.: US 10,004,675 B2
(45) Date of Patent: Jun. 26, 2018

(54) AGENT AND METHOD FOR TEMPORARY SHAPING OF KERATIN-CONTAINING FIBERS

(71) Applicant: Henkel AG & Co. KGaA, Duesseldorf (DE)

(72) Inventors: Thorsten Knappe, Schenfeld (DE); Pamela Kaftan, Hamburg (DE); Maria Catalina Bermudez Agudelo, Hamburg (DE); Tim Bethge, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days. days.

(21) Appl. No.: 15/360,250

(22) Filed: Nov. 23, 2016

(65) Prior Publication Data
US 2017/0165177 A1 Jun. 15, 2017

(30) Foreign Application Priority Data

Dec. 15, 2015 (DE) .................... 10 2015 225 201

(51) Int. Cl.
| | |
|---|---|
| A61K 8/81 | (2006.01) |
| A61K 8/04 | (2006.01) |
| A61K 8/31 | (2006.01) |
| A61K 8/33 | (2006.01) |
| A61K 8/34 | (2006.01) |
| A61Q 5/06 | (2006.01) |
| B65D 83/14 | (2006.01) |

(52) U.S. Cl.
CPC ............ *A61K 8/8158* (2013.01); *A61K 8/042* (2013.01); *A61K 8/046* (2013.01); *A61K 8/31* (2013.01); *A61K 8/315* (2013.01); *A61K 8/33* (2013.01); *A61K 8/34* (2013.01); *A61K 8/8152* (2013.01); *A61Q 5/06* (2013.01); *A61K 2800/48* (2013.01); *A61K 2800/594* (2013.01); *A61K 2800/87* (2013.01); *B65D 83/752* (2013.01)

(58) Field of Classification Search
CPC .......... A61K 2800/48; A61K 2800/594; A61K 2800/87; A61K 8/042; A61K 8/046; A61K 8/31; A61K 8/315; A61K 8/33; A61K 8/34; A61K 8/8152; A61K 8/8158; A61Q 5/06
See application file for complete search history.

(56) References Cited

U.S. PATENT DOCUMENTS

| | | | | |
|---|---|---|---|---|
| 4,874,604 A | * | 10/1989 | Sramek ................. | A61K 8/046 424/47 |
| 5,176,898 A | * | 1/1993 | Goldberg ............... | A61K 8/585 424/47 |
| 2008/0178899 A1 | * | 7/2008 | Moenks ................. | A61K 8/046 132/203 |

FOREIGN PATENT DOCUMENTS

| | | |
|---|---|---|
| DE | 102004040172 A1 | 3/2006 |
| DE | 102014217207 A1 | 3/2016 |
| EP | 1726331 A1 | 5/2005 |
| EP | 1719499 A1 | 11/2006 |
| EP | 1719500 A1 | 11/2006 |
| WO | 2005012588 A1 | 2/2005 |
| WO | 2012054278 A2 | 4/2012 |

OTHER PUBLICATIONS

Preliminary Amendment for U.S. Appl. No. 15/378,705, dated Dec. 14, 2016.
Substitute Specification for U.S. Appl. No. 15/378,705, dated Dec. 14, 2016.
Intellectual Property Office, Combined Search and Examination Report under Sections 17 and 18(3) for United Kingdom Application No. GB1621172.4 issued Oct. 2, 2017.
The DOW Chemical Company, "ACUDYNE Hair Styling Polymers Product Overview," May 2015, pp. 1-4, retrieved from the internet on Jan. 31, 2018 at: http://msdssearch.dow.com/PublishedLiteratureDOWCOM/dh_0933/0901b80380933ea9.pdf?filepath=personalcare/pdfs/noreg/324-00624.pdf&fromPage=GetDoc.

* cited by examiner

*Primary Examiner* — Ernst V Arnold
(74) *Attorney, Agent, or Firm* — Lorenz & Kopf, LLP

(57) ABSTRACT

Cosmetic agents and methods for temporarily shaping keratin-containing fibers using the cosmetic agents are provided herein. In one embodiment, a cosmetic agent for temporarily shaping keratinic fibers includes a cosmetic preparation. The cosmetic preparation contains at least one copolymer a1) composed of at least the following monomer units: (meth)acrylic acid, (meth)acrylic acid alkyl ester, and (meth)acrylic acid hydroxyalkyl ester. The cosmetic preparation further contains at least one copolymer a2) composed of at least the following monomer units: N-tert-octylacrylamide, acrylic acid, and ethyl acrylate. The amount by weight of copolymers a1) and a2) in the total weight of the cosmetic preparation amounts to about 1.0 to about 10 by weight.

20 Claims, No Drawings

AGENT AND METHOD FOR TEMPORARY SHAPING OF KERATIN-CONTAINING FIBERS

CROSS-REFERENCE TO RELATED APPLICATION

This application claims priority to German Patent Application No. 10 2015 225 201.9, filed Dec. 15, 2015, which is incorporated herein by reference in its entirety.

TECHNICAL FIELD

This disclosure relates to a cosmetic composition for setting hair and/or for temporary shaping of keratinic fibers, in particular human hair, wherein the composition contains a combination of two specific copolymers.

BACKGROUND

Temporary shaping of hair styles for a longer period of time up to several days usually requires the use of active setting agents. Therefore, hair treatment agents that serve to temporarily impart a shape to hair play an important role. Corresponding agents for temporary shaping usually contain synthetic polymers and/or waxes as the active setting agent. Agents to support the temporary shaping of keratin-containing fibers may be fabricated as hair spray, hair wax, hair gel or hair mousse, for example.

The most important properties of an agent for temporary shaping of hair, hereinafter also referred to as styling agents, consists of imparting the strongest possible hold to the treated fibers in the newly modeled shape—i.e., a shape imposed on the hair. We also speak of a strong hair style hold or a high degree of hold of the styling agent. The hair style hold is determined essentially by the type and amount of active setting agents used, but there may also be an influence of the additional ingredients of the styling agent.

In addition to a high degree of hold, styling agents must meet a number of other requirements. These can be divided roughly into properties involving the hair, properties involving the respective formulation, e.g., properties of sprayed aerosols and properties pertaining to the handling of the styling agent, wherein the properties involving the hair are particularly important. Moisture resistance, low tackiness (tack) and a balanced conditioning effect can be mentioned in particular. In addition a styling agent should be as uniformly usable as possible for all types of hair and should be mild on both hair and skin.

To do justice to the different requirements, a number of synthetic polymers that are used in styling agents have already been developed. These polymers can be divided into cationic, anionic nonionic and amphoteric setting polymers.

European Patents EP 1719499 B1, EP 1719500 B1 and EP 1726331 B1 describe acrylate resins bearing the INCI designations acrylates/hydroxy ester acrylates copolymer and their use in styling agents. International patent application WO 2012/054278 A2 also mentions acrylates/hydroxy ester acrylates copolymers as hair setting polymers and uses Acudyne® 1000 (The Dow Chemical Company) in hair mousses.

Hair sprays based on copolymers of N-tert-butylacrylamide, acrylic acid and ethyl acrylate are described in German Patent Application DE 10 2004 040 172 A1, among others.

Not all polymers and not all polymer blends are fundamentally suitable for production of hair styling agents. This is true in particular of hair sprays in which the viscosity, for example, and thus also the spray behavior are influenced by the polymer and/or the amount of polymer used.

Although suitable polymers and polymer combinations for use in the field of temporary hair styling were developed a long time ago, the results achieved so far still leave room for improvement, in particular with regard to stability in storage, applicability and the degree of hold of these agents. In particular, the styling agents currently available can still be improved to the extent that a good combination of degree of hold and long-term hold (high humidity curl retention) is not always adequately insured.

BRIEF SUMMARY

Cosmetic agents and methods for temporarily shaping keratin-containing fibers using the cosmetic agents are provided herein. In one embodiment, a cosmetic agent for temporarily shaping keratinic fibers includes a cosmetic preparation. The cosmetic preparation contains at least one copolymer a1) composed of at least the following monomer units: (meth)acrylic acid, (meth)acrylic acid alkyl ester, and (meth)acrylic acid hydroxyalkyl ester. The cosmetic preparation further contains at least one copolymer a2) composed of at least the following monomer units: N-tert-octylacrylamide, acrylic acid, and ethyl acrylate. The amount by weight of copolymers a1) and a2) in the total weight of the cosmetic preparation amounts to about 1.0 to about 10 by weight.

In another embodiment, a method for temporarily shaping keratin-containing fibers includes the step of loading keratin-containing fibers with a cosmetic agent. The cosmetic agent contains at least one copolymer a1) composed of at least the following monomer units: (meth)acrylic acid, (meth)acrylic acid alkyl ester, and (meth)acrylic acid hydroxyalkyl ester. The cosmetic product further includes at least one copolymer a2) composed of at least the following monomer units: N-tert-octylacrylamide, acrylic acid, and ethyl acrylate. The amount by weight of copolymers a1) and a2) in the total weight of the cosmetic preparation amounts to about 1.0 to about 10 by weight. The method further includes the step of temporarily fixing the keratin-containing fibers into shape.

DETAILED DESCRIPTION

The following detailed description is merely exemplary in nature and is not intended to limit the invention or the application and uses of the invention. Furthermore, there is not intention to be bound by any theory presented in the preceding background or the following detained description.

It is contemplated herein to make available additional suitable polymer combinations which are characterized by good film-forming properties and/or setting properties, have a very high degree of hold without sacrificing flexibility and good moisture resistance—in particular, perspiration resistance and water resistance. The polymer combinations should also be suitable for producing cosmetic compositions having a high chemical and physical stability and they should be simple to apply.

This has been achieved as contemplated herein through a combination of two different specific copolymers. The present disclosure makes available:

1. A cosmetic agent for temporary shaping of keratinic fibers, comprising
a) a cosmetic preparation containing
  a1) at least one copolymer which is made up of at least the following monomer units:

(meth)acrylic acid
(meth)acrylic acid alkyl ester
(meth)acrylic acid hydroxyalkyl ester;
a2) at least one copolymer made up of at least the following monomer units:
N-tert-butylacrylamide
acrylic acid
ethyl acrylate,
wherein the amount by weight of copolymers a1) and a2) in the total weight of the cosmetic preparation is about 1.0 to about 10% by weight.

2. Cosmetic agents according to point 1, wherein the amount by weight of copolymers a1) and a2) in the total weight of the cosmetic preparation is about 1.5 and about 9.0% by weight and in particular about 2.0 to about 8.0% by weight.

3. Cosmetic agent according to any one of the preceding points, wherein the at least one copolymer a1) consists of, based on its total weight, at least 90% by weight, preferably at least 95% by weight and in particular at least 97% by weight of the monomers
(meth)acrylic acid
(meth)acrylic acid alkyl ester
(meth)acrylic acid hydroxyalkyl ester.

4. Cosmetic agent according to any one of the preceding points, wherein the copolymer a1) has the INCI designation acrylates/hydroxy esters acrylates copolymer.

5. Cosmetic agent according to any one of the preceding points, wherein the preparation contains, based on its total weight, about 0.1 to about 9.9% by weight, preferably about 0.5 to about 8.5% by weight and in particular about 1.0 to about 7.0% by weight of copolymer a1).

6. Cosmetic agent according to any one of the preceding points, wherein the at least one copolymer a2), based on its total weight, contains at least 90% by weight, preferably at least 95% by weight and in particular at least 97% by weight of the monomers
N-tert-butylacrylamide
acrylic acid
ethyl acrylate.

7. Cosmetic agent according to any one of the preceding points, wherein the copolymer a2) has the INCI designation acrylates/t-butylacrylamide copolymer.

8. Cosmetic agent according to any one of the preceding points, wherein the preparation contains based on its total weight about 0.1 to about 9.9% by weight, preferably about 0.5 to about 8.5% by weight and in particular about 1.0 to about 7.0% by weight copolymer a2).

9. Cosmetic agent according to any one of the preceding points, wherein the weight ratio of copolymer a1) to copolymer a2) is from about 1:7 to about 7:1, preferably from about 1:5 to about 5:1 and in particular from about 1:3 to about 3:1.

10. Cosmetic agent according to any one of the preceding points, wherein the preparation contains based on the total weight about 40 to about 98% by weight, preferably about 60 to about 95% by weight and in particular about 70 to about 92% by weight polar solvent.

11. Cosmetic agent according to any one of the preceding points, wherein the preparation contains based on the total weight at least 70% by weight, preferably at least 80% by weight and in particular at least 90% by weight of the copolymers a1) and a2), ethanol and/or water.

12. Cosmetic agent according to any one of the preceding points, wherein the cosmetic preparation additionally comprises at least one thickener, preferably from the group of organic polymeric thickeners.

13. Cosmetic agent according to any one of the preceding points, wherein the cosmetic preparation additionally comprises at least one thickener from the group of organic anionic polymeric thickeners.

14. Cosmetic agent according to any one of the preceding points, wherein the cosmetic preparation additionally comprises at least one thickener from the group of anionic polymeric amphiphilic thickeners.

15. Cosmetic agent according to any one of the preceding points, wherein the cosmetic preparation additionally comprises at least one thickener from the group with the INCI designations acrylates/beheneth-25 methacrylate copolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer and acrylates/steareth-50 acrylate copolymer.

16. Cosmetic agent according to any one of the preceding points, wherein the preparation contains, based on its total weight, about 0.05 to about 8.0 by weight, preferably about 0.1 to about 5.0% by weight thickener.

17. Cosmetic agent according to any one of the preceding points, wherein the agent additionally comprises
b) at least one propellant.

18. Cosmetic agent according to any one of the preceding points, wherein the agent additionally comprises
b) at least one propellant from the group of propane, mixture of propane and butane, dimethyl ether and 1,1-difluoroethane.

19. Cosmetic agent according to any one of the preceding points comprising, based on its total weight
a) 30 to 70% by weight of the cosmetic preparation
b) 30 to 70% by weight propellant.

20. Cosmetic agent, comprising
i) a cosmetic agent according to any one of points 1 to 19
ii) a dispensing device with a spray valve.

21. Use of an agent or a product according to any one of points 1 to 20 for temporary shaping of keratin-containing fibers, in particular human hair.

22. Method for temporary shaping of keratin-containing fibers, in particular human hair, in which the keratinic fibers are treated with a cosmetic agent according to any one of points 1 to 20 and are temporarily set in their shape.

It has surprisingly been found that, within the scope of the present disclosure, an improved moisture resistance of styling products can be achieved by combining two ingredients that are known per se and are already used in styling products. Other properties usually required of styling products such as long-term hold, stiffness and low tack are retained or improved. Such a good combination of properties was not to be expected even with knowledge of the individual component and was therefore surprising. It was found experimentally that by combining the two components, a highly hyperadditive, i.e., synergistic effect was obtained with regard to the moisture resistance and the degree of hold.

As contemplated herein, the term "keratinic fibers" includes skins, furs, wool and feathers, but human hair in particular.

The essential ingredients of the cosmetic composition as contemplated herein include the anionic copolymer a1) and the anionic copolymer a2) that is different from copolymer a1).

The cosmetic preparations as contemplated herein contain an anionic copolymer a1) as the first essential ingredient.

With respect to the manufacturability, applicability and cosmetic effect of the cosmetic agents as contemplated herein, it has proven to be advantageous if the amount by weight of the copolymer a1) in the total weight of the cosmetic preparation amounts to a) about 0.1 to about 9.9% by weight, preferably about 0.5 to about 8.5% by weight and in particular about 1.0 to about 7.0% by weight.

The copolymer a1) can be traced back to the monomers (meth)acrylic acid, (meth)acrylic acid alkyl ester and (meth) acrylic acid hydroxyalkyl ester as well as optionally other monomers.

Preferred copolymers a1) preferably consist of at least 90% by weight, preferably at least 95% by weight and in particular at least 97% by weight of the monomers (meth) acrylic acid, (meth)acrylic acid alkyl ester and (meth)acrylic acid hydroxyalkyl ester. Especially preferred copolymers a1) were obtained exclusively from the monomers (meth) acrylic acid, (meth)acrylic acid alkyl ester and (meth)acrylic acid hydroxyalkyl ester.

The cosmetic agents of another preferred embodiment are characterized in that the at least one copolymer a1) contains, based on its total weight, at least 90% by weight, preferably at least 95% by weight and in particular at least 97% by weight of the monomers
(meth)acrylic acid
(meth)acrylic acid alkyl ester
(meth)acrylic acid hydroxyalkyl ester.

The at least one methacrylic acid may be methacrylic acid or acrylic acid.

The alkyl radical of the (meth)acrylic acid alkyl ester is preferably a $C_1$-$C_8$ alkyl radical, which may be linear or branched. Examples of alkyl radicals include methyl, ethyl, isopropyl, 1-butyl, 2-butyl, isobutyl, tert-butyl, linear or branched pentyl, linear or branched hexyl, linear or branched heptyl and linear or branched octyl. More preferably, the alkyl group is a $C_1$ to $C_5$ alkyl group. According to one embodiment of the disclosure, two or more (meth) acrylic acid alkyl esters are contained therein, differing with regard to the number of carbon atoms in the alkyl group. For example, a methacrylic acid $C_1$-$C_3$ alkyl ester and an acrylic acid $C_2$-$C_5$ alkyl ester are contained therein.

The hydroxyalkyl radical of the (meth)acrylic acid alkyl ester may be a hydroxy $C_1$-$C_{10}$ alkyl radical, preferably a hydroxy $C_2$-$C_5$ alkyl radical. In one preferred embodiment, the (meth)acrylic acid hydroxyalkyl ester unit is a (meth) acrylic acid hydroxyethyl ester.

The amount of the units (meth)acrylic acid, (meth)acrylic acid alkyl ester and (meth)acrylic acid hydroxyalkyl ester in the acrylate resin a1) may vary within wide limits. The amount of (meth)acrylic acid in the acrylate copolymer is preferably about 2 to about 50% by weight, more preferably about 5 to about 30% by weight. The amount of (meth) acrylic acid alkyl ester in the acrylate copolymer is preferably about 5 to about 95% by weight, more preferably about 45 to about 90% by weight. The amount of (meth)acrylic acid hydroxyalkyl ester in the acrylate copolymer is preferably about 2 to about 70% by weight, more preferably about 5 to about 30% by weight.

The weight-average molecular weight of the anionic acrylate copolymer a1) is preferably about 130,000 to about 160,000, more preferably about 140,000 to about 150,000, determined by means of gel permeation chromatography (GPC).

The viscosity of the anionic acrylate copolymer a1) used in the cosmetic composition is preferably at most 150 cPS (Brookfield LV, spindle 1, 60 rpm) with a solids content of about 44% to about 46% by weight and a pH of about 3.30 to about 4.30 at 25° C.

The copolymers a1) described previously are distributed by Rohm & Haas, for example, under the designation Acudyne® 1000 (INCI designation: acrylates/hydroxy esters acrylates copolymer).

The cosmetic preparations as contemplated herein contain as the second essential ingredient an anionic copolymer a2).

With respect to the manufacturability, applicability and cosmetic effect of cosmetic agents as contemplated herein, it has proven advantageous if the amount by weight of the copolymer a2) in the total weight of the cosmetic preparation a) amounts to about 0.1 to about 9.9% by weight, preferably about 0.5 to about 8.5% by weight and in particular about 1.0 to about 7.0% by weight.

The copolymer a2) can be traced back to the N-tert-butylacrylamide, acrylic acid and ethyl acrylate monomers and optionally additional monomers.

Preferred copolymers a2) preferably consist of at least 90% by weight, preferably at least 95% by weight and in particular at least 97% by weight of the monomers i) N-tert-butylacrylamide, ii) acrylic acid, iii) ethyl acrylate. Especially preferred copolymers a2) were obtained exclusively from the monomers i) N-tert-butylacrylamide, ii) acrylic acid, iii) ethyl acrylate.

The copolymers a2) described previously are distributed, for example, under the designation Ultrahold® 8 (INCI designation: acrylates/t-butylacrylamide copolymer, CAS number 26062-56-6) by BASF.

The copolymer a2) is preferably used in a neutralized or partially neutralized form in the cosmetic agents. Preferably at least one alkanolamine is used for neutralization. The alkanolamines that can be used as the alkalizing agent as contemplated herein are preferably selected from primary amines with a $C_2$-$C_6$ alkyl backbone, having at least one hydroxyl group. Especially preferred alkanolamines are selected from the group formed from 2-aminoethan-1-ol (monoethanolamine), tris(2-hydroxyethyl)-amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol. As contemplated herein most especially preferred alkanolamines are selected from the group 2-aminoethan-1-ol, 2-amino-2-methylpropan-1-ol and 2-amino-2-methylpropane-1,3-diol. 2-Amino-2-methylpropanol has proven to be a particularly suitable neutralizing agent. Cosmetic agents preferred as contemplated herein contain at least one alkanolamine preferably 2-amino-2-methylpropanol. The 2-amino-2-methylpropanol is used in the agents as contemplated herein, preferably in an amount not exceeding the amount required for neutralization of the copolymer a2). The amounts of 2-amino-2-methylpropanol used in the agents as contemplated herein are preferably about 80 to 100%, especially preferably about 90 to 100% and in particular about 95 to 100% of the amount required for complete neutralization of the copolymer a2). In a preferred embodiment the amount by weight of the 2-amino-2-methylpropanol of the total weight of the cosmetic preparation a) amounts to about 0.1 to about 4.0% by weight, preferably about 0.5 to about 3.0% by weight and in particular about 1.0 to about 2.0% by weight.

The amount by weight of copolymers a1) and a2) in the total weight of the cosmetic preparation amounts to about 1.0 to about 10% by weight. Cosmetic preparations in which the amount by weight of copolymers a1) and a2) of the total weight of the cosmetic preparation is about 1.5 and about 9.0% by weight and in particular about 2.0 to about 8.0% by weight are preferred.

In addition to the total amount by weight of copolymers a1) and a2), the weight ratio of copolymers a1) and a2) to one another also has an influence on the moisture resistance, the degree of hold and the additional use properties of the cosmetic agents as contemplated herein. Technically especially advantageous cosmetic agents are characterized in that the weight ratio of copolymer a1) to copolymer a2) is from about 1:7 to about 7:1, preferably from about 1:5 to about 5:1 and in particular from about 1:3 to about 3:1.

In addition to the copolymers a1) and copolymers a2) described previously, the cosmetic preparations as contemplated herein may contain additional active ingredients, additives and care substances.

The film-forming polymers form a first group of active ingredients that are preferably used. These film-forming polymers are not identical to the copolymer a1) or copolymer a2) described above. The amount by weight of the film-forming polymer in the total weight of the cosmetic preparation preferably amounts to about 0.1 to about 8.0% by weight, preferably about 0.5 to about 6.0% by weight and in particular about 1.0 to about 4.0% by weight.

Nonionic polymers are especially preferably used as the film-forming polymers. Suitable nonionic polymers include, for example:

Vinyl pyrrolidone/vinyl ester copolymers, such as those distributed under the brand name Luviskol® (BASF). Luviskol® VA 64 and Luviskol® VA 73, each of which is a vinyl pyrrolidone/vinyl acetate copolymer, are preferably nonionic polymers.
Cellulose ethers such as hydroxypropyl cellulose, hydroxyethyl cellulose and methyl hydroxypropyl cellulose such as those distributed under the brand names Culminal® and Benecel® (AQUALON).
Shellac
Polyvinyl pyrrolidones such as those distributed under the designation Luviskol® (BASF), for example.
Siloxanes. These siloxanes may be both water soluble and water insoluble. Both volatile and nonvolatile siloxanes are suitable, wherein nonvolatile siloxanes are understood to be compounds having a boiling point above 200° C. under normal pressure. Preferred siloxanes include polydialkylsiloxanes such as, for example, polydimethylsiloxane, polyalkylarylsiloxanes such as, for example, polyphenylmethylsiloxane, ethoxylated polydialkylsiloxanes and polydialkylsiloxanes containing amine groups and/or hydroxyl groups.
Glycosidically substituted silicones.

Film-forming polymers that are preferably used as contemplated herein because of their cosmetic effect in combination with the copolymers a1) and a2) as contemplated herein, include in particular the polyvinyl pyrrolidones (INCI designation PVP) as well as the vinyl pyrrolidone/vinyl acetate copolymers (INCI designation VP/VA copolymer), wherein the amount by weight of these polymers is preferably limited to amounts between 1.0 and 10% by weight. Especially preferred cosmetic preparations as contemplated herein are therefore characterized in that they additionally contain, based on their total weight, 1.0 to 10% by weight polyvinyl pyrrolidone and/or vinyl pyrrolidone/vinyl acetate copolymer, preferably polyvinyl pyrrolidone. Especially preferred cosmetic preparations have an amount by weight of the polyvinyl pyrrolidone and/or vinyl pyrrolidone/vinyl acetate copolymer in the total weight of the cosmetic preparation of 2.0 to 8.5% by weight, preferably from 3.0 to 7.0% by weight.

In summary, the cosmetic agents that are especially preferred as contemplated herein contain three different polymers with the copolymers a1) and a2) and the film-forming polymer a3).

Protein hydrolyzates and/or their derivatives may be used as the care substance. Protein hydrolyzates are product mixtures obtained by acidic, basic or enzymatically catalyzed degradation of proteins. The concept of protein hydrolyzates is also understood as contemplated herein to include total hydrolyzates as well as individual amino acids and their derivatives as well as mixtures of different amino acids. The molecular weight of the protein hydrolyzates that can be used as contemplated herein is between about 75, the molecular weight of glycine, and about 200,000, but the molecular weight is preferably about 75 to about 50,000 and most especially preferably about 75 to about 20,000 Dalton.

Another group of care substances includes vitamins, provitamins, vitamin precursors and/or derivatives thereof. Such vitamins, provitamins and vitamin precursors that are usually assigned to the groups A, B, C, E, F and H are preferred as contemplated herein.

Additional care substances include glycerin, propylene glycol, panthenol, caffeine, nicotinamide and sorbitol.

Plant extracts, but also monosaccharides and/or oligosaccharides and/or lipids, may also be used as the care substance.

The composition of some cosmetic preparations a) in which the amount by weight of the copolymers a1) and a2) in the total weight of the cosmetic preparation is about 1.0 to about 10% by weight, preferably about 1.5 to about 9.0% by weight and in particular about 2.0 to about 8.0% by weight can be derived from the following tables (the amounts in % by weight relate to the total weight of the cosmetic agent unless otherwise indicated).

|  | Formula 1 | Formula 2 | Formula 3 | Formula 4 | Formula 5 |
| --- | --- | --- | --- | --- | --- |
| Copolymer a1)* | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Optional additive | to 100 | to 100 | to 100 | to 100 | to 100 |

|  | Formula 6 | Formula 7 | Formula 8 | Formula 9 | Formula 10 |
| --- | --- | --- | --- | --- | --- |
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Optional additive | to 100 | to 100 | to 100 | to 100 | to 100 |

-continued

|  | Formula 11 | Formula 12 | Formula 13 | Formula 14 | Formula 15 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Optional additive | to 100 | to 100 | to 100 | to 100 | to 100 |

|  | Formula 16 | Formula 17 | Formula 18 | Formula 19 | Formula 20 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Optional additive | to 100 | to 100 | to 100 | to 100 | to 100 |

*according to claim 1

The cosmetic preparations as contemplated herein can be finished in various ways. The amount by weight and the exact composition of the liquid vehicle optionally contained in the cosmetic preparation have an important influence on the final finished form of these preparations.

Preferred cosmetic agents are based on an aqueous, aqueous/alcoholic or alcoholic vehicle. Thus preferred cosmetic agents contain, based on their total weight about 40 to about 98% by weight, preferably about 60 to about 95% by weight and in particular about 70 to about 92% by weight polar solvent, preferably a polar solvent from the group of water, ethanol and isopropanol.

As already mentioned, the lower alcohols with 1 to 4 carbon atoms, such as ethanol and isopropanol, for example, which are usually used for cosmetic purposes in particular, may also be included.

In addition to these alcoholic solvents, water-soluble cosolvents may also be used in particular in combination with water. Examples of especially preferred cosolvents include glycerin and/or ethylene glycol and/or 1,2-propylene glycol, which are preferably used in an amount of 0 to about 30% by weight, based on the cosmetic preparation a).

Together with the copolymers a1) and a2) described further above, the aqueous, aqueous/alcoholic or alcoholic vehicles preferably form an important ingredient of the cosmetic preparations a) as contemplated herein. Especially preferred are cosmetic preparations which consist of, based on their total weight, at least 70% by weight, preferably at least 80% by weight and in particular at least 90% by weight of the copolymers a1) and a2), ethanol and/or water.

The composition of some technical advantageous cosmetic preparations a) with a liquid vehicle in which the amount by weight of the copolymers a1) and a2) in the total weight of the cosmetic preparation amounts to about 1.0 to about 10% by weight, preferably about 1.5 to about 9.0% by weight and in particular about 2.0 to about 8.0% by weight can be taken from the following tables. (The amounts in % by weight are based on the total weight of the cosmetic agent, unless otherwise indicated.)

|  | Formula 21 | Formula 22 | Formula 23 | Formula 24 | Formula 25 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additive | to 100 | to 100 | to 100 | to 100 | to 100 |

|  | Formula 26 | Formula 27 | Formula 28 | Formula 29 | Formula 30 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additive | to 100 | to 100 | to 100 | to 100 | to 100 |

|  | Formula 31 | Formula 32 | Formula 33 | Formula 34 | Formula 35 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additive | to 100 | to 100 | to 100 | to 100 | to 100 |

|  | Formula 36 | Formula 37 | Formula 38 | Formula 39 | Formula 40 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Water and/or ethanol | 40 to 98 | 40 to 98 | 60 to 95 | 60 to 95 | 70 to 92 |
| Optional additive | to 100 | to 100 | to 100 | to 100 | to 100 |

*according to claim 1

Not only can the amount by weight of the liquid vehicle in the total weight of the cosmetic preparation a) be varied, but the weight ratio of the aqueous vehicle to the alcoholic vehicle can of course also be varied.

The composition of some technical advantageous cosmetic preparations a) with a liquid vehicle in which the amount by weight of copolymers a1) and a2) in the total weight of the cosmetic preparation amounts to about 1.0 to about 10% by weight, preferably about 1.5 to about 9.0% by weight and in particular about 2.0 to about 8.0% by weight can be taken from the following tables. (The amounts in % by weight are based on the total weight of the cosmetic agent, unless otherwise indicated.) Corresponding cosmetic preparations are suitable as pump sprays, for example.

Cosmetic Preparations a) with a High Ethanol Content

|  | Formula 41 | Formula 42 | Formula 43 | Formula 44 | Formula 45 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additive | to 100 | to 100 | to 100 | to 100 | to 100 |

|  | Formula 46 | Formula 47 | Formula 48 | Formula 49 | Formula 50 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additive | to 100 | to 100 | to 100 | to 100 | to 100 |

|  | Formula 51 | Formula 52 | Formula 53 | Formula 54 | Formula 55 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additive | to 100 | to 100 | to 100 | to 100 | to 100 |

|  | Formula 56 | Formula 57 | Formula 58 | Formula 59 | Formula 60 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Ethanol | 60 to 98 | 60 to 98 | 60 to 98 | 60 to 98 | 60 to 98 |
| Water | 0 to 10 | 0 to 10 | 0 to 10 | 0 to 10 | 0 to 10 |
| Optional additive | to 100 | to 100 | to 100 | to 100 | to 100 |

Cosmetic Preparations a) with an Average Ethanol Content

|  | Formula 61 | Formula 62 | Formula 63 | Formula 64 | Formula 65 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additive | to 100 | to 100 | to 100 | to 100 | to 100 |

|  | Formula 66 | Formula 67 | Formula 68 | Formula 69 | Formula 70 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additive | to 100 | to 100 | to 100 | to 100 | to 100 |

|  | Formula 71 | Formula 72 | Formula 73 | Formula 74 | Formula 75 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additive | to 100 | to 100 | to 100 | to 100 | to 100 |

-continued

|  | Formula 76 | Formula 77 | Formula 78 | Formula 79 | Formula 80 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Ethanol | 10 to 50 | 15 to 50 | 20 to 50 | 25 to 50 | 30 to 50 |
| Water | 2.0 to 40 | 2.0 to 40 | 2.0 to 40 | 2.0 to 40 | 2.0 to 40 |
| Optional additive | to 100 | to 100 | to 100 | to 100 | to 100 |

Cosmetic Preparations a) with a Low Ethanol Content

|  | Formula 81 | Formula 82 | Formula 83 | Formula 84 | Formula 85 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additive | to 100 | to 100 | to 100 | to 100 | to 100 |

|  | Formula 86 | Formula 87 | Formula 88 | Formula 89 | Formula 90 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additive | to 100 | to 100 | to 100 | to 100 | to 100 |

|  | Formula 91 | Formula 92 | Formula 93 | Formula 94 | Formula 95 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additive | to 100 | to 100 | to 100 | to 100 | to 100 |

|  | Formula 96 | Formula 97 | Formula 98 | Formula 99 | Formula 100 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Ethanol | 0 to 20 | 0 to 20 | 0 to 20 | 0 to 5.0 | 0 to 5.0 |
| Water | 50 to 97 | 60 to 97 | 60 to 97 | 65 to 97 | 65 to 97 |
| Optional additive | to 100 | to 100 | to 100 | to 100 | to 100 |

*according to claim 1

Conceivable fabricated forms for cosmetic preparations a) as contemplated herein include creams and lotions but also gels. In addition, however, these preparations are also suitable for use as mousse, foam or spray.

Cosmetic gel preparations contain at least one thickener as an additional ingredient. With respect to the manufacturability, applicability and cosmetic effect of cosmetic compositions as contemplated herein, it has proven advantageous if the amount by weight of thickener a2) in the total weight of the cosmetic preparation a) amounts to about 0.05 to about 8.0% by weight, preferably about 0.1 to about 5.0% by weight.

Preferred thickeners are selected from the group of organic polymeric thickeners. The organic polymeric thickeners may be crosslinked or uncrosslinked.

Preferred thickeners are selected from the group of organic anionic polymeric thickeners. A first group of especially preferred thickeners a2) contain at least one structural unit selected from at least one structural unit of formula (I) or their salt forms or at least one structural unit (II) or its salt forms:

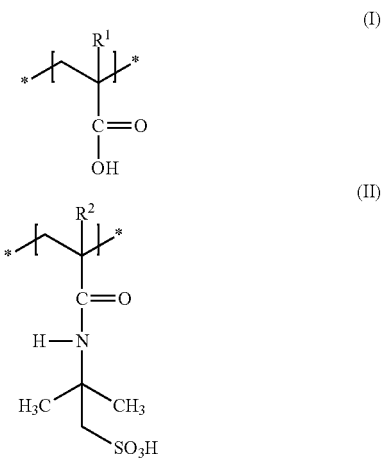

wherein $R^1$ and $R^2$, independently of one another, stand for a hydrogen atom or a methyl group.

According to the above formulas and all following formulas, a chemical bond which is indicated with the symbol * stands for a free valence of the corresponding structure fragments.

Especially preferred anionic polymers that have a thickening effect contain at least one structural unit of formula (I). Acrylic acid homopolymers form a first group of especially preferred thickeners.

Especially preferred thickeners include
polyacrylic acids with the INCI designation carbomer such as those distributed by the company 3V Sigma under the brand names Synthalen® K or by the company Lubrizol under the brand name Carbopol.

A second especially preferred group of thickeners a2) is the anionic, polymeric, amphiphilic thickeners. Corresponding thickeners include preferably at least one structural unit of formula (III) and at least one structural unit of formula (IV)

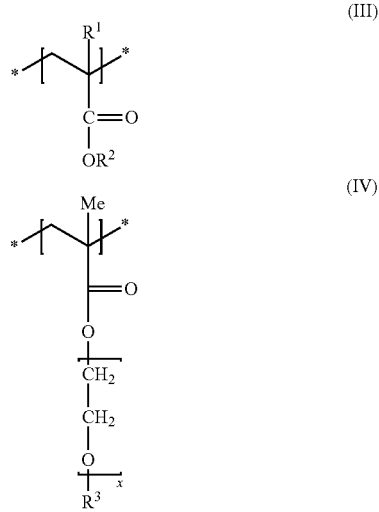

wherein
$R^1$ stands for a hydrogen atom or a methyl group
$R^2$ stands for a hydrogen atom or a ($C_1$ to $C_6$) alkyl group
$R^3$ stands for a ($C_8$ to $C_{30}$) alkyl group
$M^+$ stands for a physiologically tolerable cation and
x stands for an integer from 0 to 35.

Preferred thickeners are in particular those with the INCI designations acrylates/beheneth-25 methacrylate copolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer and acrylates/steareth-50 acrylate copolymer.

Especially preferred thickeners are
Thickeners with the INCI designation acrylates/steareth-20 methacrylate copolymer such as those distributed by the company Rohm & Haas under the brand name Aculyn® 22, for example;
Thickeners with the INCI designation acrylates/steareth-20 methacrylate crosspolymer such as those distributed by the company Rohm & Haas under the brand name Aculyn® 88, for example;
Thickeners with the INCI designation acrylates/steareth-20 itaconate copolymer such as those distributed by the company National Starch under the brand name Structure 2001, for example.

Additional anionic polymeric amphiphilic thickeners are characterized by long-chain alkyl substituents. This group includes, for example, the compounds with the INCI designations acrylates/stearyl methacrylate copolymer, acrylates/vinyl isodecanoate crosspolymer.

Especially preferred thickeners include:
thickeners with the INCI designation acrylates/$C_{10-30}$ alkyl acrylate crosspolymer, such as those distributed by the company Lubrizol under the brand name Carbopol Ultrez 21, for example.

Additional thickeners can be selected from the polymeric thickeners known by the following INCI designations, for example: acrylamides copolymer, acrylamide/sodium acrylate copolymer, acrylamide/sodium acryloyldimethyl taurate copolymer, acrylates/acetoacetoxyethyl methacrylate copolymer, acrylic acid/acrylonitrogens copolymer, agar, agarose, *alcaligenes* polysaccharides, algin, alginic acid, ammonium acrylates/acrylonitrogens copolymer, ammonium acrylates copolymer, ammonium acryloyldimethyl taurate/vinylformamide copolymer, ammonium acryloyldimethyl taurate/VP copolymer, ammonium alginate, ammonium polyacryloyldimethyl taurate, amylopectin, ascorbyl methylsilanol pectinate, *astragalus gummifer* gum, attapulgite, *Avena sativa* (oat) kernel flour, bentonite, butoxy chitosan, *Caesalpinia spinosa* gum, calcium alginate, calcium carboxymethylcellulose, calcium carrageenan, calcium potassium carbomer, calcium starch octenyl succinate, $C_{20-40}$ alkyl stearate, carboxybutyl chitosan, carboxymethyl chitin, carboxymethyl chitosan, carboxymethyl dextran, carboxymethyl hydroxyethylcellulose, carboxymethyl hydroxypropyl guar, cellulose acetate propionate carboxylate, cellulose gum, *Ceratonia siliqua* gum, cetyl hydroxyethylcellulose, cholesterol/HDI/pullulan copolymer, cholesteryl hexyl dicarbamate pullulan, *Cyamopsis tetragonoloba* (guar) gum, diglycol/CHDM/isophthalates/SIP copolymer, dihydrogenated tallow benzylmonium hectorite, dimethicone crosspolymer-2, dimethicone propyl PG-betaine, DMAPA acrylates/acrylic acid/acrylonitrogens copolymer, ethylene/sodium acrylate copolymer, gelatin, gellan gum, glyceryl alginate, *glycine soja* (soybean) flour, guar hydroxypropyltrimonium chloride, hectorite, hydrated silica, hydrogenated potato starch, hydroxybutyl methylcellulose, hydroxyethyl acrylate/sodium acryloyldimethyl taurate copolymer, hydroxyethylcellulose, hydroxyethyl chitosan, hydroxyethyl ethylcellulose, hydroxypropylcellulose, hydroxypropyl chitosan, hydroxypropyl ethylenediamine carbomer, hydroxypropyl guar, hydroxypropyl methylcellulose, hydroxypropyl methylcellulose stearoxy ether, hydroxystearamide MEA, isobutylene/sodium maleate copolymer, lithium magnesium silicate, lithium magnesium sodium silicate, *Macrocystis pyrifera* (kelp), magnesium alginate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, montmorillonite, Moroccan lava clay, natto gum, nonoxynyl hydroxyethylcellulose, octadecene/MA copolymer, pectin, PEG-800, PEG-crosspolymer, PEG-150/decyl alcohol/SMDI copolymer, PEG-175 diisostearate, PEG-190 distearate, PEG-15 glyceryl tristearate, PEG-140 glyceryl tristearate, PEG-240/HDI copolymer bis-decyltetradeceth-20 ether, PG-100/IPDI copolymer, PEG-180/laureth-50/TMMG copolymer, PEG-10/lauryl dimethicone crosspolymer, PEG-15/lauryl dimethicone crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 methyl glucose trioleate, PEG-180/ octoxynol-40/TMMG copolymer, PEG-150 pentaerythrityl tetrastearate, PEG-4 rapeseed amide, PEG-150/stearyl alcohol/SMDI copolymer, polyacrylate-3, polyacrylic acid, polycyclopentadiene, polyether-1, polyethylene/isopropyl maleate/MA copolyol, polymethacrylic acid, polyquaternium-52, polyvinyl alcohol, potassium alginate, potassium aluminum polyacrylate, potassium carbomer, potassium carrageenan, potassium polyacrylate, potato starch modified, PPG-14 laureth-60 hexyl dicarbamate, PPG-14 laureth-60 isophoryl dicarbamate, PPG-14 palmeth-60 hexyl dicarbamate, propylene glycol alginate, PVP/decene copolymer, PVP montmorillonite, rhizobian gum, ricinoleic acid/adipic acid/AEEA copolymer, *sclerotium* gum, sodium acrylate/acryloyldimethyl taurate copolymer, sodium acrylates/acrolein copolymer, sodium acrylates/acrylonitrogens copolymer, sodium acrylates copolymer, sodium acrylates/vinyl isodecanoate crosspolymer, sodium acrylate/vinyl alcohol copolymer, sodium carbomer, sodium carboxymethyl chitin, sodium carboxymethyl dextran, sodium carboxymethyl beta-glucan, sodium carboxymethyl starch, sodium carrageenan, sodium cellulose sulfate, sodium cyclodextrin sulfate, sodium hydroxypropyl starch phosphate, sodium isooctylene/MA copolymer, sodium magnesium fluorosilicate, sodium polyacrylate, sodium polyacrylate starch, sodium polyacryloyldimethyl taurate, sodium polymethacrylate, sodium polystyrene sulfonate, sodium silicoaluminate, sodium starch octenylsuccinate, sodium stearoxy PG-hydroxyethylcellulose sulfonate, sodium styrene/acrylates copolymer, sodium tauride acrylates/acrylic acid/acrylonitrogens copolymer, *solanum tuberosum* (potato) starch, starch/acrylates/acrylamide copolymer, starch hydroxypropyltrimonium chloride, steareth-60 cetyl ether, steareth-100/PEG-136/HDI copolymer, *Sterculia urens* gum, synthetic fluorphlogopite, *Tamarindus indica* seed gum, tapioca starch, TEA alginate, TEA carbomer, *Triticum vulgare* (wheat) starch, trometamine acrylates/acrylonitrogens copolymer, trometamine magnesium aluminum silicate, Welan gum, yeast beta-glucan, yeast polysaccharides, *Zea mays* (corn) starch.

The composition of some technically advantageous cosmetic preparations a) with a liquid vehicle, in which the amount by weight of copolymers a1) and a2) in the total weight of the cosmetic preparation amounts to about 1.0 to about 10% by weight, preferably about 1.5 to about 9.0% by weight and in particular about 2.0 to about 8.0% by weight can be taken from the following tables. (The amounts in % by weight are based on the total weight of the cosmetic agent, unless otherwise indicated.)

|  | Formula 101 | Formula 102 | Formula 103 | Formula 104 | Formula 105 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Organic polymeric thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additive | to 100 | to 100 | to 100 | to 100 | to 100 |

|  | Formula 106 | Formula 107 | Formula 108 | Formula 109 | Formula 110 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Copolymer a2)* | 0.1 to 9.9 | 0.1 to 8.9 | 0.5 to 8.0 | 0.5 to 7.5 | 1.0 to 7.0 |
| Organic polymeric thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additive | to 100 | to 100 | to 100 | to 100 | to 100 |

|  | Formula 111 | Formula 112 | Formula 113 | Formula 114 | Formula 115 |
|---|---|---|---|---|---|
| Copolymer a1)* | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Organic polymeric thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additive | to 100 | to 100 | to 100 | to 100 | to 100 |

|  | Formula 116 | Formula 117 | Formula 118 | Formula 119 | Formula 120 |
|---|---|---|---|---|---|
| Acrylates/hydroxy esters acrylates copolymer (INCI) | 0.1 to 9.9 | 0.1 to 8.9 | 0.5 to 8.0 | 0.5 to 7.5 | 1.0 to 7.0 |
| Acrylates/t-butylacrylamide copolymer (INCI) | 0.1 to 9.9 | 0.1 to 8.9 | 0.5 to 8.0 | 0.5 to 7.5 | 1.0 to 7.0 |
| Organic polymeric thickener | 0.05 to 8.0 | 0.05 to 8.0 | 0.1 to 5.0 | 0.1 to 5.0 | 0.1 to 5.0 |
| Water and/or ethanol | 40 to 98 | 40 to 98 | 60 to 95 | 60 to 95 | 70 to 92 |
| Optional additive | to 100 | to 100 | to 100 | to 100 | to 100 |

*according to claim 1

The mousse, foam or spray can be supplied without the addition of a propellant, for example, by means of a mechanical pump, foam or spray device, but also with the use of a propellant (e.g., aerosol spray). Corresponding cosmetic agents then additionally include at least one propellant b) in addition to the cosmetic preparation a).

Suitable propellants (propellant gases) include propane, propene, n-butane, isobutane, isobutene, n-pentane, pentene, isopentane, isopentene, methane, ethane, dimethyl ether, nitrogen, air, oxygen, nitrous oxide, 1,1,1,3-tetrafluorethane, heptafluoro-n-propane, perfluoroethane, monochlorodifluoromethane, 1,1-difluoroethane, namely both individually and in combination. Hydrophilic propellant gases such as carbon dioxide, for example, may also be used advantageously in the sense of the present disclosure if the amount of hydrophilic gases selected is low and lipophilic propellant gas (for example, propane/butane) is present in excess. Especially preferred are propane, n-butane, isobutane and mixtures of these propellant gases. Preferred cosmetic agents are characterized in that the agent additionally comprises at least one propellant b) from the group propane, mixture of propane and butane, dimethyl ether and 1,1-difluoroethane (INCI: hydrofluorocarbon 152a).

The additional composition of some preferred cosmetic agents, which also comprise, in addition to the cosmetic preparation a), a propellant b), and in which the amount by weight of copolymers a1) and a2) in the total weight of the cosmetic preparation amount to about 1.0 to about 10% by weight, preferably about 1.5 to about 9.0% by weight and in particular about 2.0 to about 8.0% by weight can be taken from the following Tables 1 and 2.

Some preferred cosmetic agents containing cosmetic preparation a) and propellant b) are described in the following Tables 1 and 2.

Table 1 shows cosmetic agents with a low propellant content (e.g., mousses), while Table 2 shows cosmetic agents with a high propellant content (e.g., sprays).

In Tables 1 and 2, the left column ("formula x") refers to one of the cosmetic preparations a) of formulas 1 to 100 listed as an example in the tables disclosed above. The additional columns 2 to 5 ("propellant") indicate the combined amount of propellant with the corresponding cosmetic preparation. These amounts in "wt %" are based on the total weight of the cosmetic preparation a) of the respective "formula x" without propellant.

The statement "4 to 12.5% by weight" in the following Table 1 thus corresponds to the addition of propellant to the cosmetic preparation a) in an amount of about 4 to about 12.5% by weight of the weight of the cosmetic preparation a). In other words, the cosmetic preparation a) and the propellant b) are present in this cosmetic agent in a weight ratio of about 100:4 to about 100:12.5 and/or from about 25:1 to about 8:1.

In other words, the cosmetic agents according to line 2, column 4 in Table 1 below are mixtures of the propellant-free cosmetic preparation a) according to formula 1 of the above table with propane/butane in a weight ratio of about 100:4 to about 100:12.5 or, in other words, a cosmetic agent for temporary shaping of keratinic fibers, comprising
a) a cosmetic preparation, containing
  a1) about 0.1 to about 9.9% by weight of at least one copolymer which is made up of at least the following monomer units:
    (meth)acrylic acid
    (meth)acrylic acid alkyl ester
    (meth)acrylic acid hydroxyalkyl ester;
  a2) about 0.1 to about 9.9% by weight of at least one copolymer made up of at least the following monomer units:
    N-tert-butylacrylamide
    acrylic acid
    ethyl acrylate
b) propellant from the group of propane/butane r, wherein the amount by weight of copolymers a1) and a2) in the total weight of the cosmetic preparation amounts to about 1.0 to about 10% by weight and the weight ratio of the cosmetic preparation a) to the propellant b) amounts to about 25:1 to about 8:1.

A first group of especially preferred cosmetic agents as contemplated herein contains, based on their total weight, about 80 to about 96% by weight of the cosmetic preparation a) as well as about 4 to about 20% by weight propellant, preferably about 87.5 to about 96% by weight of the cosmetic preparation a) and 4 to 12.5% by weight propellant b) and in particular about 92 to about 96% by weight of the cosmetic preparation a) as well as about 4 to about 8% by weight propellant. Preferred propellants include propane/butane mixtures. Corresponding agents are suitable in particular for use as mousse or foam:

TABLE 1

| | Propellant (% by weight) | | | |
|---|---|---|---|---|
| Formula 1 | 4 to 20 | 4 to 20 P/B* | 4 to 12.5 P/B* | 4 to 8 P/B* |
| Formula 2 | 4 to 20 | 4 to 20 P/B* | 4 to 12.5 P/B* | 4 to 8 P/B* |
| Formula 3 | 4 to 20 | 4 to 20 P/B* | 4 to 12.5 P/B* | 4 to 8 P/B* |
| Formula 4 | 4 to 20 | 4 to 20 P/B* | 4 to 12.5 P/B* | 4 to 8 P/B* |
| Formula 5 | 4 to 20 | 4 to 20 P/B* | 4 to 12.5 P/B* | 4 to 8 P/B* |
| Formula 6 | 4 to 20 | 4 to 20 P/B* | 4 to 12.5 P/B* | 4 to 8 P/B* |
| Formula 7 | 4 to 20 | 4 to 20 P/B* | 4 to 12.5 P/B* | 4 to 8 P/B* |
| Formula 8 | 4 to 20 | 4 to 20 P/B* | 4 to 12.5 P/B* | 4 to 8 P/B* |
| Formula 9 | 4 to 20 | 4 to 20 P/B* | 4 to 12.5 P/B* | 4 to 8 P/B* |
| Formula 10 | 4 to 20 | 4 to 20 P/B* | 4 to 12.5 P/B* | 4 to 8 P/B* |
| Formula 11 | 4 to 20 | 4 to 20 P/B* | 4 to 12.5 P/B* | 4 to 8 P/B* |
| Formula 12 | 4 to 20 | 4 to 20 P/B* | 4 to 12.5 P/B* | 4 to 8 P/B* |
| Formula 13 | 4 to 20 | 4 to 20 P/B* | 4 to 12.5 P/B* | 4 to 8 P/B* |
| Formula 14 | 4 to 20 | 4 to 20 P/B* | 4 to 12.5 P/B* | 4 to 8 P/B* |
| Formula 15 | 4 to 20 | 4 to 20 P/B* | 4 to 12.5 P/B* | 4 to 8 P/B* |
| Formula 16 | 4 to 20 | 4 to 20 P/B* | 4 to 12.5 P/B* | 4 to 8 P/B* |
| Formula 17 | 4 to 20 | 4 to 20 P/B* | 4 to 12.5 P/B* | 4 to 8 P/B* |
| Formula 18 | 4 to 20 | 4 to 20 P/B* | 4 to 12.5 P/B* | 4 to 8 P/B* |
| Formula 19 | 4 to 20 | 4 to 20 P/B* | 4 to 12.5 P/B* | 4 to 8 P/B* |
| Formula 20 | 4 to 20 | 4 to 20 P/B* | 4 to 12.5 P/B* | 4 to 8 P/B* |
| Formula 21 | 4 to 20 | 4 to 20 P/B* | 4 to 12.5 P/B* | 4 to 8 P/B* |
| Formula 22 | 4 to 20 | 4 to 20 P/B* | 4 to 12.5 P/B* | 4 to 8 P/B* |
| Formula 23 | 4 to 20 | 4 to 20 P/B* | 4 to 12.5 P/B* | 4 to 8 P/B* |
| Formula 24 | 4 to 20 | 4 to 20 P/B* | 4 to 12.5 P/B* | 4 to 8 P/B* |
| Formula 25 | 4 to 20 | 4 to 20 P/B* | 4 to 12.5 P/B* | 4 to 8 P/B* |
| Formula 26 | 4 to 20 | 4 to 20 P/B* | 4 to 12.5 P/B* | 4 to 8 P/B* |
| Formula 27 | 4 to 20 | 4 to 20 P/B* | 4 to 12.5 P/B* | 4 to 8 P/B* |
| Formula 28 | 4 to 20 | 4 to 20 P/B* | 4 to 12.5 P/B* | 4 to 8 P/B* |
| Formula 29 | 4 to 20 | 4 to 20 P/B* | 4 to 12.5 P/B* | 4 to 8 P/B* |
| Formula 30 | 4 to 20 | 4 to 20 P/B* | 4 to 12.5 P/B* | 4 to 8 P/B* |
| Formula 31 | 4 to 20 | 4 to 20 P/B* | 4 to 12.5 P/B* | 4 to 8 P/B* |
| Formula 32 | 4 to 20 | 4 to 20 P/B* | 4 to 12.5 P/B* | 4 to 8 P/B* |
| Formula 33 | 4 to 20 | 4 to 20 P/B* | 4 to 12.5 P/B* | 4 to 8 P/B* |
| Formula 34 | 4 to 20 | 4 to 20 P/B* | 4 to 12.5 P/B* | 4 to 8 P/B* |
| Formula 35 | 4 to 20 | 4 to 20 P/B* | 4 to 12.5 P/B* | 4 to 8 P/B* |
| Formula 36 | 4 to 20 | 4 to 20 P/B* | 4 to 12.5 P/B* | 4 to 8 P/B* |
| Formula 37 | 4 to 20 | 4 to 20 P/B* | 4 to 12.5 P/B* | 4 to 8 P/B* |
| Formula 38 | 4 to 20 | 4 to 20 P/B* | 4 to 12.5 P/B* | 4 to 8 P/B* |
| Formula 39 | 4 to 20 | 4 to 20 P/B* | 4 to 12.5 P/B* | 4 to 8 P/B* |
| Formula 40 | 4 to 20 | 4 to 20 P/B* | 4 to 12.5 P/B* | 4 to 8 P/B* |
| Formula 41 | 4 to 20 | 4 to 20 P/B* | 4 to 12.5 P/B* | 4 to 8 P/B* |
| Formula 42 | 4 to 20 | 4 to 20 P/B* | 4 to 12.5 P/B* | 4 to 8 P/B* |
| Formula 43 | 4 to 20 | 4 to 20 P/B* | 4 to 12.5 P/B* | 4 to 8 P/B* |
| Formula 44 | 4 to 20 | 4 to 20 P/B* | 4 to 12.5 P/B* | 4 to 8 P/B* |
| Formula 45 | 4 to 20 | 4 to 20 P/B* | 4 to 12.5 P/B* | 4 to 8 P/B* |
| Formula 46 | 4 to 20 | 4 to 20 P/B* | 4 to 12.5 P/B* | 4 to 8 P/B* |
| Formula 47 | 4 to 20 | 4 to 20 P/B* | 4 to 12.5 P/B* | 4 to 8 P/B* |
| Formula 48 | 4 to 20 | 4 to 20 P/B* | 4 to 12.5 P/B* | 4 to 8 P/B* |
| Formula 49 | 4 to 20 | 4 to 20 P/B* | 4 to 12.5 P/B* | 4 to 8 P/B* |
| Formula 50 | 4 to 20 | 4 to 20 P/B* | 4 to 12.5 P/B* | 4 to 8 P/B* |
| Formula 51 | 4 to 20 | 4 to 20 P/B* | 4 to 12.5 P/B* | 4 to 8 P/B* |
| Formula 52 | 4 to 20 | 4 to 20 P/B* | 4 to 12.5 P/B* | 4 to 8 P/B* |
| Formula 53 | 4 to 20 | 4 to 20 P/B* | 4 to 12.5 P/B* | 4 to 8 P/B* |
| Formula 54 | 4 to 20 | 4 to 20 P/B* | 4 to 12.5 P/B* | 4 to 8 P/B* |
| Formula 55 | 4 to 20 | 4 to 20 P/B* | 4 to 12.5 P/B* | 4 to 8 P/B* |
| Formula 56 | 4 to 20 | 4 to 20 P/B* | 4 to 12.5 P/B* | 4 to 8 P/B* |
| Formula 57 | 4 to 20 | 4 to 20 P/B* | 4 to 12.5 P/B* | 4 to 8 P/B* |
| Formula 58 | 4 to 20 | 4 to 20 P/B* | 4 to 12.5 P/B* | 4 to 8 P/B* |
| Formula 59 | 4 to 20 | 4 to 20 P/B* | 4 to 12.5 P/B* | 4 to 8 P/B* |

TABLE 1-continued

| | Propellant (% by weight) | | | |
|---|---|---|---|---|
| Formula 60 | 4 to 20 | 4 to 20 P/B* | 4 to 12.5 P/B* | 4 to 8 P/B* |
| Formula 61 | 4 to 20 | 4 to 20 P/B* | 4 to 12.5 P/B* | 4 to 8 P/B* |
| Formula 62 | 4 to 20 | 4 to 20 P/B* | 4 to 12.5 P/B* | 4 to 8 P/B* |
| Formula 63 | 4 to 20 | 4 to 20 P/B* | 4 to 12.5 P/B* | 4 to 8 P/B* |
| Formula 64 | 4 to 20 | 4 to 20 P/B* | 4 to 12.5 P/B* | 4 to 8 P/B* |
| Formula 65 | 4 to 20 | 4 to 20 P/B* | 4 to 12.5 P/B* | 4 to 8 P/B* |
| Formula 66 | 4 to 20 | 4 to 20 P/B* | 4 to 12.5 P/B* | 4 to 8 P/B* |
| Formula 67 | 4 to 20 | 4 to 20 P/B* | 4 to 12.5 P/B* | 4 to 8 P/B* |
| Formula 68 | 4 to 20 | 4 to 20 P/B* | 4 to 12.5 P/B* | 4 to 8 P/B* |
| Formula 69 | 4 to 20 | 4 to 20 P/B* | 4 to 12.5 P/B* | 4 to 8 P/B* |
| Formula 70 | 4 to 20 | 4 to 20 P/B* | 4 to 12.5 P/B* | 4 to 8 P/B* |
| Formula 71 | 4 to 20 | 4 to 20 P/B* | 4 to 12.5 P/B* | 4 to 8 P/B* |
| Formula 72 | 4 to 20 | 4 to 20 P/B* | 4 to 12.5 P/B* | 4 to 8 P/B* |
| Formula 73 | 4 to 20 | 4 to 20 P/B* | 4 to 12.5 P/B* | 4 to 8 P/B* |
| Formula 74 | 4 to 20 | 4 to 20 P/B* | 4 to 12.5 P/B* | 4 to 8 P/B* |
| Formula 75 | 4 to 20 | 4 to 20 P/B* | 4 to 12.5 P/B* | 4 to 8 P/B* |
| Formula 76 | 4 to 20 | 4 to 20 P/B* | 4 to 12.5 P/B* | 4 to 8 P/B* |
| Formula 77 | 4 to 20 | 4 to 20 P/B* | 4 to 12.5 P/B* | 4 to 8 P/B* |
| Formula 78 | 4 to 20 | 4 to 20 P/B* | 4 to 12.5 P/B* | 4 to 8 P/B* |
| Formula 79 | 4 to 20 | 4 to 20 P/B* | 4 to 12.5 P/B* | 4 to 8 P/B* |
| Formula 80 | 4 to 20 | 4 to 20 P/B* | 4 to 12.5 P/B* | 4 to 8 P/B* |
| Formula 81 | 4 to 20 | 4 to 20 P/B* | 4 to 12.5 P/B* | 4 to 8 P/B* |
| Formula 82 | 4 to 20 | 4 to 20 P/B* | 4 to 12.5 P/B* | 4 to 8 P/B* |
| Formula 83 | 4 to 20 | 4 to 20 P/B* | 4 to 12.5 P/B* | 4 to 8 P/B* |
| Formula 84 | 4 to 20 | 4 to 20 P/B* | 4 to 12.5 P/B* | 4 to 8 P/B* |
| Formula 85 | 4 to 20 | 4 to 20 P/B* | 4 to 12.5 P/B* | 4 to 8 P/B* |
| Formula 86 | 4 to 20 | 4 to 20 P/B* | 4 to 12.5 P/B* | 4 to 8 P/B* |
| Formula 87 | 4 to 20 | 4 to 20 P/B* | 4 to 12.5 P/B* | 4 to 8 P/B* |
| Formula 88 | 4 to 20 | 4 to 20 P/B* | 4 to 12.5 P/B* | 4 to 8 P/B* |
| Formula 89 | 4 to 20 | 4 to 20 P/B* | 4 to 12.5 P/B* | 4 to 8 P/B* |
| Formula 90 | 4 to 20 | 4 to 20 P/B* | 4 to 12.5 P/B* | 4 to 8 P/B* |
| Formula 91 | 4 to 20 | 4 to 20 P/B* | 4 to 12.5 P/B* | 4 to 8 P/B* |
| Formula 92 | 4 to 20 | 4 to 20 P/B* | 4 to 12.5 P/B* | 4 to 8 P/B* |
| Formula 93 | 4 to 20 | 4 to 20 P/B* | 4 to 12.5 P/B* | 4 to 8 P/B* |
| Formula 94 | 4 to 20 | 4 to 20 P/B* | 4 to 12.5 P/B* | 4 to 8 P/B* |
| Formula 95 | 4 to 20 | 4 to 20 P/B* | 4 to 12.5 P/B* | 4 to 8 P/B* |
| Formula 96 | 4 to 20 | 4 to 20 P/B* | 4 to 12.5 P/B* | 4 to 8 P/B* |
| Formula 97 | 4 to 20 | 4 to 20 P/B* | 4 to 12.5 P/B* | 4 to 8 P/B* |
| Formula 98 | 4 to 20 | 4 to 20 P/B* | 4 to 12.5 P/B* | 4 to 8 P/B* |
| Formula 99 | 4 to 20 | 4 to 20 P/B* | 4 to 12.5 P/B* | 4 to 8 P/B* |
| Formula 100 | 4 to 20 | 4 to 20 P/B* | 4 to 12.5 P/B* | 4 to 8 P/B* |

*"P/B" corresponds to a propane/butane mixture

The statement "50 to 200% by weight" in Table 2 below corresponds to the addition of propellant to the cosmetic preparation a) in an amount of about 50 to about 200% by weight of the weight of the cosmetic preparation a). In other words, the cosmetic preparation a) and the propellant b) are present in this cosmetic agent in a weight ratio of about 100:50 to about 100:20 and/or from about 2:1 to about 1:2.

In line 4, column 3 in the following Table 2, a mixture of the propellant-free cosmetic preparation a) according to formula 3 with a propane/butane mixture is described. The entry in line 4, column 3 thus describes a cosmetic agent for temporary shaping of keratinic fibers, comprising:

a) a cosmetic preparation containing
    a1) about 0.5 to about 8.0% by weight of at least one copolymer made up of at least the following monomer units:
        (meth)acrylic acid
        (meth)acrylic acid alkyl ester
        (meth)acrylic acid hydroxyalkyl ester;
    a2) about 0.5 to about 8.0% by weight of at least one copolymer made up of at least the following monomer units:
        N-tert-butylacrylamide
        acrylic acid
        ethyl acrylate, b) propellant from the group of propane/butane mixtures, wherein the amount by weight of the copolymers a1) and a2) in the total weight of the cosmetic preparation amounts to about 1.0 to about 10% by weight and the weight ratio of the cosmetic preparation a) to propellant b) amounts to about 2:1 to about 1:2.

A second group of particularly preferred cosmetic agents as contemplated herein contains, based on its total weight, about 30 to about 70% by weight of the cosmetic preparation a) and about 30 to about 70% by weight propellant b). Such agents are suitable in particular for use as a spray:

TABLE 2

| | Propellant (% by weight) | | | |
|---|---|---|---|---|
| Formula 1 | 50 to 200 | 50 to 200 P/B* | 50 to 200 DFE** | 50 to 200 DME*** |
| Formula 2 | 50 to 200 | 50 to 200 P/B* | 50 to 200 DFE** | 50 to 200 DME*** |
| Formula 3 | 50 to 200 | 50 to 200 P/B* | 50 to 200 DFE** | 50 to 200 DME*** |
| Formula 4 | 50 to 200 | 50 to 200 P/B* | 50 to 200 DFE** | 50 to 200 DME*** |
| Formula 5 | 50 to 200 | 50 to 200 P/B* | 50 to 200 DFE** | 50 to 200 DME*** |
| Formula 6 | 50 to 200 | 50 to 200 P/B* | 50 to 200 DFE** | 50 to 200 DME*** |
| Formula 7 | 50 to 200 | 50 to 200 P/B* | 50 to 200 DFE** | 50 to 200 DME*** |
| Formula 8 | 50 to 200 | 50 to 200 P/B* | 50 to 200 DFE** | 50 to 200 DME*** |
| Formula 9 | 50 to 200 | 50 to 200 P/B* | 50 to 200 DFE** | 50 to 200 DME*** |
| Formula 10 | 50 to 200 | 50 to 200 P/B* | 50 to 200 DFE** | 50 to 200 DME*** |
| Formula 11 | 50 to 200 | 50 to 200 P/B* | 50 to 200 DFE** | 50 to 200 DME*** |
| Formula 12 | 50 to 200 | 50 to 200 P/B* | 50 to 200 DFE** | 50 to 200 DME*** |
| Formula 13 | 50 to 200 | 50 to 200 P/B* | 50 to 200 DFE** | 50 to 200 DME*** |
| Formula 14 | 50 to 200 | 50 to 200 P/B* | 50 to 200 DFE** | 50 to 200 DME*** |
| Formula 15 | 50 to 200 | 50 to 200 P/B* | 50 to 200 DFE** | 50 to 200 DME*** |
| Formula 16 | 50 to 200 | 50 to 200 P/B* | 50 to 200 DFE** | 50 to 200 DME*** |
| Formula 17 | 50 to 200 | 50 to 200 P/B* | 50 to 200 DFE** | 50 to 200 DME*** |
| Formula 18 | 50 to 200 | 50 to 200 P/B* | 50 to 200 DFE** | 50 to 200 DME*** |
| Formula 19 | 50 to 200 | 50 to 200 P/B* | 50 to 200 DFE** | 50 to 200 DME*** |
| Formula 20 | 50 to 200 | 50 to 200 P/B* | 50 to 200 DFE** | 50 to 200 DME*** |
| Formula 21 | 50 to 200 | 50 to 200 P/B* | 50 to 200 DFE** | 50 to 200 DME*** |
| Formula 22 | 50 to 200 | 50 to 200 P/B* | 50 to 200 DFE** | 50 to 200 DME*** |
| Formula 23 | 50 to 200 | 50 to 200 P/B* | 50 to 200 DFE** | 50 to 200 DME*** |
| Formula 24 | 50 to 200 | 50 to 200 P/B* | 50 to 200 DFE** | 50 to 200 DME*** |
| Formula 25 | 50 to 200 | 50 to 200 P/B* | 50 to 200 DFE** | 50 to 200 DME*** |
| Formula 26 | 50 to 200 | 50 to 200 P/B* | 50 to 200 DFE** | 50 to 200 DME*** |
| Formula 27 | 50 to 200 | 50 to 200 P/B* | 50 to 200 DFE** | 50 to 200 DME*** |
| Formula 28 | 50 to 200 | 50 to 200 P/B* | 50 to 200 DFE** | 50 to 200 DME*** |

TABLE 2-continued

| | Propellant (% by weight) | | | |
|---|---|---|---|---|
| Formula 29 | 50 to 200 | 50 to 200 P/B* | 50 to 200 DFE** | 50 to 200 DME*** |
| Formula 30 | 50 to 200 | 50 to 200 P/B* | 50 to 200 DFE** | 50 to 200 DME*** |
| Formula 31 | 50 to 200 | 50 to 200 P/B* | 50 to 200 DFE** | 50 to 200 DME*** |
| Formula 32 | 50 to 200 | 50 to 200 P/B* | 50 to 200 DFE** | 50 to 200 DME*** |
| Formula 33 | 50 to 200 | 50 to 200 P/B* | 50 to 200 DFE** | 50 to 200 DME*** |
| Formula 34 | 50 to 200 | 50 to 200 P/B* | 50 to 200 DFE** | 50 to 200 DME*** |
| Formula 35 | 50 to 200 | 50 to 200 P/B* | 50 to 200 DFE** | 50 to 200 DME*** |
| Formula 36 | 50 to 200 | 50 to 200 P/B* | 50 to 200 DFE** | 50 to 200 DME*** |
| Formula 37 | 50 to 200 | 50 to 200 P/B* | 50 to 200 DFE** | 50 to 200 DME*** |
| Formula 38 | 50 to 200 | 50 to 200 P/B* | 50 to 200 DFE** | 50 to 200 DME*** |
| Formula 39 | 50 to 200 | 50 to 200 P/B* | 50 to 200 DFE** | 50 to 200 DME*** |
| Formula 40 | 50 to 200 | 50 to 200 P/B* | 50 to 200 DFE** | 50 to 200 DME*** |
| Formula 41 | 50 to 200 | 50 to 200 P/B* | 50 to 200 DFE** | 50 to 200 DME*** |
| Formula 42 | 50 to 200 | 50 to 200 P/B* | 50 to 200 DFE** | 50 to 200 DME*** |
| Formula 43 | 50 to 200 | 50 to 200 P/B* | 50 to 200 DFE** | 50 to 200 DME*** |
| Formula 44 | 50 to 200 | 50 to 200 P/B* | 50 to 200 DFE** | 50 to 200 DME*** |
| Formula 45 | 50 to 200 | 50 to 200 P/B* | 50 to 200 DFE** | 50 to 200 DME*** |
| Formula 46 | 50 to 200 | 50 to 200 P/B* | 50 to 200 DFE** | 50 to 200 DME*** |
| Formula 47 | 50 to 200 | 50 to 200 P/B* | 50 to 200 DFE** | 50 to 200 DME*** |
| Formula 48 | 50 to 200 | 50 to 200 P/B* | 50 to 200 DFE** | 50 to 200 DME*** |
| Formula 49 | 50 to 200 | 50 to 200 P/B* | 50 to 200 DFE** | 50 to 200 DME*** |
| Formula 50 | 50 to 200 | 50 to 200 P/B* | 50 to 200 DFE** | 50 to 200 DME*** |
| Formula 51 | 50 to 200 | 50 to 200 P/B* | 50 to 200 DFE** | 50 to 200 DME*** |
| Formula 52 | 50 to 200 | 50 to 200 P/B* | 50 to 200 DFE** | 50 to 200 DME*** |
| Formula 53 | 50 to 200 | 50 to 200 P/B* | 50 to 200 DFE** | 50 to 200 DME*** |
| Formula 54 | 50 to 200 | 50 to 200 P/B* | 50 to 200 DFE** | 50 to 200 DME*** |
| Formula 55 | 50 to 200 | 50 to 200 P/B* | 50 to 200 DFE** | 50 to 200 DME*** |
| Formula 56 | 50 to 200 | 50 to 200 P/B* | 50 to 200 DFE** | 50 to 200 DME*** |
| Formula 57 | 50 to 200 | 50 to 200 P/B* | 50 to 200 DFE** | 50 to 200 DME*** |
| Formula 58 | 50 to 200 | 50 to 200 P/B* | 50 to 200 DFE** | 50 to 200 DME*** |
| Formula 59 | 50 to 200 | 50 to 200 P/B* | 50 to 200 DFE** | 50 to 200 DME*** |
| Formula 60 | 50 to 200 | 50 to 200 P/B* | 50 to 200 DFE** | 50 to 200 DME*** |
| Formula 61 | 50 to 200 | 50 to 200 P/B* | 50 to 200 DFE** | 50 to 200 DME*** |
| Formula 62 | 50 to 200 | 50 to 200 P/B* | 50 to 200 DFE** | 50 to 200 DME*** |
| Formula 63 | 50 to 200 | 50 to 200 P/B* | 50 to 200 DFE** | 50 to 200 DME*** |
| Formula 64 | 50 to 200 | 50 to 200 P/B* | 50 to 200 DFE** | 50 to 200 DME*** |
| Formula 65 | 50 to 200 | 50 to 200 P/B* | 50 to 200 DFE** | 50 to 200 DME*** |
| Formula 66 | 50 to 200 | 50 to 200 P/B* | 50 to 200 DFE** | 50 to 200 DME*** |
| Formula 67 | 50 to 200 | 50 to 200 P/B* | 50 to 200 DFE** | 50 to 200 DME*** |
| Formula 68 | 50 to 200 | 50 to 200 P/B* | 50 to 200 DFE** | 50 to 200 DME*** |
| Formula 69 | 50 to 200 | 50 to 200 P/B* | 50 to 200 DFE** | 50 to 200 DME*** |
| Formula 70 | 50 to 200 | 50 to 200 P/B* | 50 to 200 DFE** | 50 to 200 DME*** |
| Formula 71 | 50 to 200 | 50 to 200 P/B* | 50 to 200 DFE** | 50 to 200 DME*** |
| Formula 72 | 50 to 200 | 50 to 200 P/B* | 50 to 200 DFE** | 50 to 200 DME*** |
| Formula 73 | 50 to 200 | 50 to 200 P/B* | 50 to 200 DFE** | 50 to 200 DME*** |
| Formula 74 | 50 to 200 | 50 to 200 P/B* | 50 to 200 DFE** | 50 to 200 DME*** |
| Formula 75 | 50 to 200 | 50 to 200 P/B* | 50 to 200 DFE** | 50 to 200 DME*** |
| Formula 76 | 50 to 200 | 50 to 200 P/B* | 50 to 200 DFE** | 50 to 200 DME*** |
| Formula 77 | 50 to 200 | 50 to 200 P/B* | 50 to 200 DFE** | 50 to 200 DME*** |
| Formula 78 | 50 to 200 | 50 to 200 P/B* | 50 to 200 DFE** | 50 to 200 DME*** |
| Formula 79 | 50 to 200 | 50 to 200 P/B* | 50 to 200 DFE** | 50 to 200 DME*** |
| Formula 80 | 50 to 200 | 50 to 200 P/B* | 50 to 200 DFE** | 50 to 200 DME*** |
| Formula 81 | 50 to 200 | 50 to 200 P/B* | 50 to 200 DFE** | 50 to 200 DME*** |
| Formula 82 | 50 to 200 | 50 to 200 P/B* | 50 to 200 DFE** | 50 to 200 DME*** |
| Formula 83 | 50 to 200 | 50 to 200 P/B* | 50 to 200 DFE** | 50 to 200 DME*** |
| Formula 84 | 50 to 200 | 50 to 200 P/B* | 50 to 200 DFE** | 50 to 200 DME*** |
| Formula 85 | 50 to 200 | 50 to 200 P/B* | 50 to 200 DFE** | 50 to 200 DME*** |
| Formula 86 | 50 to 200 | 50 to 200 P/B* | 50 to 200 DFE** | 50 to 200 DME*** |
| Formula 87 | 50 to 200 | 50 to 200 P/B* | 50 to 200 DFE** | 50 to 200 DME*** |
| Formula 88 | 50 to 200 | 50 to 200 P/B* | 50 to 200 DFE** | 50 to 200 DME*** |
| Formula 89 | 50 to 200 | 50 to 200 P/B* | 50 to 200 DFE** | 50 to 200 DME*** |
| Formula 90 | 50 to 200 | 50 to 200 P/B* | 50 to 200 DFE** | 50 to 200 DME*** |
| Formula 91 | 50 to 200 | 50 to 200 P/B* | 50 to 200 DFE** | 50 to 200 DME*** |
| Formula 92 | 50 to 200 | 50 to 200 P/B* | 50 to 200 DFE** | 50 to 200 DME*** |
| Formula 93 | 50 to 200 | 50 to 200 P/B* | 50 to 200 DFE** | 50 to 200 DME*** |
| Formula 94 | 50 to 200 | 50 to 200 P/B* | 50 to 200 DFE** | 50 to 200 DME*** |
| Formula 95 | 50 to 200 | 50 to 200 P/B* | 50 to 200 DFE** | 50 to 200 DME*** |
| Formula 96 | 50 to 200 | 50 to 200 P/B* | 50 to 200 DFE** | 50 to 200 DME*** |
| Formula 97 | 50 to 200 | 50 to 200 P/B* | 50 to 200 DFE** | 50 to 200 DME*** |
| Formula 98 | 50 to 200 | 50 to 200 P/B* | 50 to 200 DFE** | 50 to 200 DME*** |
| Formula 99 | 50 to 200 | 50 to 200 P/B* | 50 to 200 DFE** | 50 to 200 DME*** |
| Formula 100 | 50 to 200 | 50 to 200 P/B* | 50 to 200 DFE** | 50 to 200 DME*** |

*"P/B" corresponds to a propane/butane mixture
**"DFE" corresponds to 1,1-difluorethane
***"DME" corresponds to dimethyl ether Vessels made of metal (aluminum, white tin, tin), protected and/or shatterproof plastic or glass coated with plastic on the outside may be used as the pressurized gas containers for the aerosol applications. Compressive strength and breaking strength, corrosion resistance, ease of filling as well as aesthetic factors, handleability, printability, etc. all play a role in the choice thereof. Special internal protective paints ensure the corrosion resistance in comparison with cosmetic agents a).

If the agents as contemplated herein are to be sprayed onto hair, these agents are advantageously provided with a dispensing device and a spray valve. The resulting cosmetic products thus comprise a cosmetic agent as contemplated herein as well as a dispensing device with a spray valve.

In a preferred embodiment of the disclosure, the valve has a valve cone, which is coated with a paint or a polymeric plastic A and such a flexible element having a restoring characteristic such that their valve recoils into the closure position (=resting position of the valve) after the end of the activation. Corresponding cosmetic products in which the aerosol dispensing device comprises a valve having a valve covering and/or a flexible element having a restoring characteristic, which is/are coated with a paint or with a polymeric plastic A are preferred as contemplated herein.

In another preferred embodiment of the disclosure, the valve has a flexible element with a restoring characteristic and/or a valve cone made of at least one plastic B, preferably an elastomeric plastic. Here again, cosmetic products as contemplated herein, in which the valve has a flexible element with a restoring characteristic and/or a valve cone made of at least one plastic B, are preferred, wherein preferred plastics B are elastomeric plastics. Particularly preferred elastomeric plastics are selected from Buna, in particular Buna N, Buna 421, Buna 1602 and Buna KA 6712, neoprene, butyl and chlorobutyl.

In another preferred embodiment of the disclosure, the flexible element with a restoring characteristic may be embodied as a spiral spring and/or as a helical compression spring. In another preferred embodiment of the disclosure, a flexible element with a restoring characteristic may be designed in one piece with the valve cone and may have flexible legs.

As explained in the introduction, the cosmetic agents described above are characterized by special hair cosmetic properties, in particular advantageous properties in temporary shaping of hair. Another subject matter of the present disclosure is therefore the use of an agent as contemplated herein for temporary shaping of keratin-containing fibers, in particular human hair.

A third subject matter of the present disclosure is a method for temporary shaping of keratin-containing fibers, in particular human hair, in which the keratinic fibers are treated with a cosmetic agent as contemplated herein and are temporarily fixed in their shape.

The invention claimed is:

1. A cosmetic agent for temporary shaping of keratinic fibers, comprising:
   a cosmetic preparation containing:
      at least one copolymer a1) composed of at least the following monomer units;
         (meth)acrylic acid,
         (meth)acrylic acid alkyl ester, and
         (meth)acrylic acid hydroxyalkyl ester;
      at least one copolymer a2) composed of at least the following monomer units;
         N-tert-butylacrylamide,
         acrylic acid, and
         ethyl acrylate; and
      a film-forming polymer that is not identical to copolymer a1) or copolymer a2),
   wherein the film-forming polymer comprises a glycosidically substituted silicone;
   wherein the amount by weight of copolymers a1) and a2) in the total weight of the cosmetic preparation amounts to about 1.0 to about 10% by weight, and wherein the amount by weight of the film-forming polymer in the total weight of the cosmetic preparation is from about 0.5% to about 6.0% by weight.

2. The cosmetic agent according to claim 1, wherein the amount by weight of copolymers a1) and a2) in the total weight of the cosmetic preparation amounts to about 1.5 and about 9.0% by weight.

3. The cosmetic agent according to claim 1, wherein the preparation contains, based on its total weight, about 0.1 to about 9.9% by weight of copolymer a1).

4. The cosmetic agent according to claim 1, wherein the preparation contains based on its total weight about 0.1 to about 9.9% by weight of copolymer a2).

5. The cosmetic agent according to claim 1, wherein the weight ratio of copolymer a1) to copolymer a2) is from about 1:7 to about 7:1.

6. The cosmetic agent according to claim 1, wherein the agent additionally comprises at least one propellant.

7. The cosmetic agent according to claim 1 comprising, based on its total weight, about 30 to about 70% by weight of the cosmetic preparation, and about 30 to about 70% by weight of at least one propellant.

8. The cosmetic agent of claim 1 further comprising:
   agent according to claim 1; and
   a dispensing device with a spray valve.

9. The cosmetic agent according to claim 1, wherein the amount by weight of copolymers a1) and a2) in the total weight of the cosmetic preparation amounts to about 2.0 and about 8.0% by weight.

10. The cosmetic agent according to claim 1, wherein the preparation contains, based on its total weight, about 0.5 to about 8.5% by weight of copolymer a1).

11. The cosmetic agent according to claim 1, wherein the preparation contains, based on its total weight, about 1.0 to about 7.0% by weight of copolymer a1).

12. The cosmetic agent according to claim 1, wherein the preparation contains based on its total weight about 0.5 to about 8.5% by weight of copolymer a2).

13. The cosmetic agent according to claim 1, wherein the preparation contains based on its total weight about 1.0 to about 7.0% by weight of copolymer a2).

14. The cosmetic agent according to claim 1, wherein the weight ratio of copolymer a1) to copolymer a2) amounts to is from about 1:5 to about 5:1.

15. The cosmetic agent according to claim 1, wherein the weight ratio of copolymer a1) to copolymer a2) is from about 1:3 to about 3:1.

16. The cosmetic agent according to claim 1, wherein the copolymer a1) has the INCI designation acrylates/hydroxy esters acrylates copolymer.

17. The cosmetic agent according to claim 1, wherein the copolymer a2) has the INCI designation acrylates/t-butylacrylamide copolymer.

18. The cosmetic agent according to claim 1, wherein the cosmetic preparation additionally comprises at least one thickener from the group with the INCI designations acrylates/beheneth-25 methacrylate copolymer, acrylates/ceteth-20 itaconate copolymer, acrylates/ceteth-20 methacrylate copolymer, acrylates/laureth-25 methacrylate copolymer, acrylates/palmeth-20 acrylate copolymer, acrylates/palmeth-25 acrylate copolymer, acrylates/palmeth-25 itaconate copolymer and acrylates/steareth-50 acrylate copolymer.

19. A cosmetic agent for temporary shaping of keratinic fibers, comprising:
a cosmetic preparation containing:
at least one copolymer a1) composed of at least the following monomer units;
(meth)acrylic acid,
(meth)acrylic acid alkyl ester, and
(meth)acrylic acid hydroxyalkyl ester;
at least one copolymer a2) composed of at least the following monomer units;
N-tert-butylacrylamide,
acrylic acid, and
ethyl acrylate;
a film-forming polymer that is not identical to copolymer a1) or copolymer a2), wherein the film-forming polymer comprises a glycosidically substituted silicone;
at least one propellant from the group propane, mixture of propane and butane, dimethyl ether and 1,1-difluoroethane; and
at least one of ethanol or water;
wherein the amount by weight of copolymers a1) and a2) in the total weight of the cosmetic preparation amounts to about 1.0 to about 10% by weight, and wherein the amount by weight of the film-forming polymer in the total weight of the cosmetic preparation is from about 0.5% to about 6.0% by weight.

20. A method for temporary shaping of keratinic fibers, the method comprising the steps of:
loading keratin-containing fibers with a cosmetic agent comprising:
at least one copolymer a1) that is constructed from at least the following monomer units;
(meth)acrylic acid,
(meth)acrylic acid alkyl ester, and
(meth)acrylic acid hydroxyalkyl ester; and
at least one copolymer a2) that is constructed from at least the following monomer units;
N-tert-butylacrylamide,
acrylic acid, and
ethyl acrylate;
a film-forming polymer that is not identical to copolymer a1) or copolymer a2), wherein the film-forming polymer comprises a glycosidically substituted silicone;
wherein the amount by weight of copolymers a1) and a2) in the total weight of the cosmetic agent amounts to about 1.0 to about 10% by weight, and wherein the amount by weight of the film-forming polymer in the total weight of the cosmetic preparation is from about 0.5% to about 6.0% by weight; and
temporarily fixing the keratin-containing fibers into shape.

* * * * *